Figure 1:
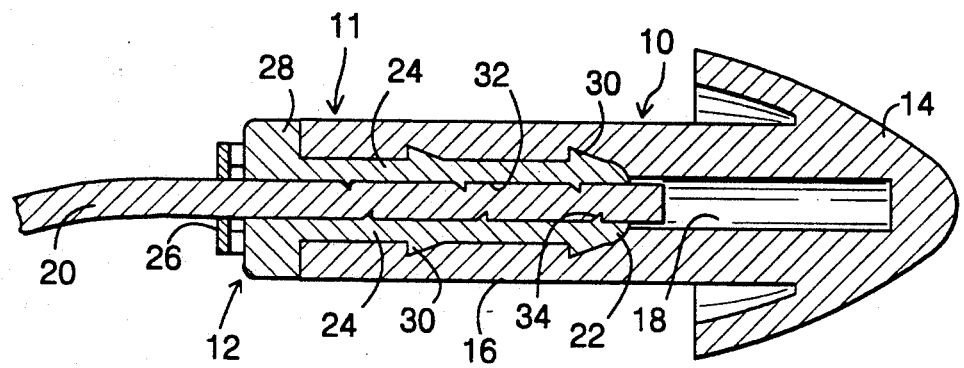

United States Patent
Berg et al.

[11] Patent Number: 5,249,309
[45] Date of Patent: Oct. 5, 1993

[54] EAR DEFENDER

[75] Inventors: Göran Berg, Tyringe; Niclas Lundblad, Angelholm, both of Sweden

[73] Assignee: Bilsom AB, Billesholm, Sweden

[21] Appl. No.: 946,388

[22] Filed: Sep. 17, 1992

[51] Int. Cl.$^5$ .............................................. A42B 1/06
[52] U.S. Cl. ...................................... 2/209; 128/865
[58] Field of Search .................... 2/209, 423; 128/864, 128/865, 868; 606/109

[56] References Cited

U.S. PATENT DOCUMENTS

| | | | |
|---|---|---|---|
| 2,441,866 | 5/1948 | Cantor | 2/209 |
| 2,619,960 | 12/1952 | Reynolds | 128/868 |
| 2,824,558 | 2/1958 | Michael | 128/865 |
| 3,097,643 | 7/1963 | Santi | 2/209 |
| 3,123,069 | 3/1964 | Laisne | 128/865 |
| 4,490,857 | 1/1985 | Leight | 2/209 |
| 4,671,265 | 6/1987 | Andersson | 2/209 |

Primary Examiner—Clifford D. Crowder
Assistant Examiner—Diana L. Biefeld
Attorney, Agent, or Firm—Michael, Best & Friedrich

[57] ABSTRACT

An ear defender which comprises two ear plugs (11) each of which is connected to a respective end of a cord (20). Each plug (11) includes a plug-part (10) which is provided with a recess (18) for a cord locking sleeve which coacts with a respective plug-part. The locking sleeve (12) is slotted from its front end in the plug-part so as to form two identical sleeve-parts (24). These are joined together at the rear end of the locking sleeve (12) by at least one hinge or web part (26) formed integrally with the locking sleeve. A length of the end of the cord extends into a channel (32) in the sleeve through an opening provided in the vicinity of the hinge part. The cord end is secured in the channel (32), by pressing the sleeve parts into firm engagement with the cord end within the recess (18).

15 Claims, 1 Drawing Sheet

EAR DEFENDER

The present invention relates to an ear defender which comprises two ear lugs each of which is connected to a respective end of a cord and includes a plug-part which is provided with a recess for accommodating a cord locking sleeve which coacts with a respective plug-part.

One such ear defender is known, for instance, from European Patent Application No. 87303472.2. The ear plugs of the ear defender described in this earlier publication are constructed so that if lost, they can be found with the aid of a metal detector. Each plug is connected to the cord with the aid of a metal sleeve which is squeezed or pinched onto respective ends of the cord. The sleeve is then inserted into and held by the plug-part.

The object of the invention is to provide an improved ear defender of the aforesaid kind in which the sleeves are secured to respective ends of the cord and the plug-parts are secured to respective sleeves more securely.

A further object of the invention is to configure the components of the ear defender in a way which will enable the ear defender to be assembled simply and easily.

The novel ear defender is mainly characterized in that each locking sleeve is slotted from its front end, i.e. from that end which projects into the plug-part, so as to form two identical sleeve-parts which are joined or held together at the rear end of the locking sleeve by at least one web part which forms a hinge and which is integral with the locking sleeve, wherein a length of the end of the cord extends into a channel in the sleeve through an opening provided in the vicinity of said hinge part and wherein said cord end is secured in the channel, by pressing the sleeve parts into firm engagement with said cord end within the recess.

Further characteristic features of the invention will be apparent from the depending claims.

Figure 2:
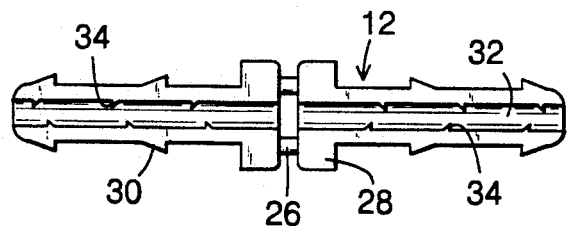
Figure 3:
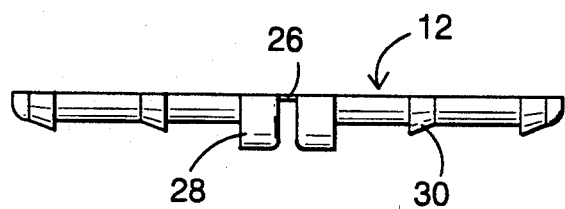

The novel ear defender will now be described in more detail with reference to a preferred exemplifying embodiment thereof and also with reference to the accompanying drawings, in which FIG. 1 is a sectioned view of an inventive ear defender plug connected to one end part of a cord;

FIG. 2 is a top view of the locking sleeve belonging to the lug and shows said sleeve immediately after manufacture; and FIG. 3 is a side view of the sleeve shown in FIG. 2.

The ear plug shown in FIG. 1 consists of two parts, namely a plug-part 10 and a locking sleeve 12. The plug-part is preferably made of rubber or a rubber-like material, such as a plastic material and preferably a silicone plastic. The locking sleeve is preferably made of a somewhat harder material, preferably also a plastic material, e.g. polypropylene.

The front end 14 of the plug-part 10 is conical in shape or rounded so as to provide a good fit in the outer part of the auditory duct of the ear. Projecting outwardly from the rear part of the conical end 14 is a shaft part 16 which is provided with a recess 18 which is initially open at the rear.

The locking sleeve is configured so as to be a good fit in the recess 18 of the plug-part 10 and also to be able to hold securely the respective end of the cord 20. The front end 22 of the locking sleeve 12 is slightly conical in shape, so that said sleeve can be readily inserted into the plug-part 10 when assembling the ear defender. Insertion is also facilitated due to the fact that, as before mentioned, the sleeve 12 is made of a somewhat harder material than the plug-part 10. The locking sleeve comprises two identical sleeve-parts 24, which are held together by two hinge parts or webs 26 formed integrally with said parts (see in particular FIGS. 2 and 3). The rear end of the sleeve 12 is widened slightly and forms an abutment means 28 which limits the extent to which the sleeve 12 can be inserted into the recess 18. The sleeve 12 is provided externally with outwardly projecting barbs 30, which extend peripherally around the sleeve and bite into the softer material of the lug-part 10 and therewith prevent unintentional separation of the locking sleeve 12 from the plug-part 10. As will be seen from FIG. 1, that part of the sleeve 12 which extends into the plug-part 10 has a slightly larger diameter than the recess 18, which will, of course, improve the holding effect obtained between the plug-part 10 and the sleeve 12. Each of the two hinge parts or webs lies on a respective side of the cord 20. The inner channel 32 of the sleeve 12 is provided with inwardly facing projections 34 which are intended to prevent unintentional separation of the cord 20 from the sleeve 12 when the latter is inserted in the recess 18. As will be seen from FIG. 1, the end of the cord passes completely through the sleeve 12 and extends slightly from the front part 22 thereof. The extent to which the cord extends from the front part 22 of the sleeve is not critical, since the depth of the recess 18 forwards of the sleeve 12 is well adapted.

The locking sleeve 12 is preferably a one-piece structure and will suitably have the form shown in FIGS. 2 and 3. The two sleeve parts 24 are then bent together at the hinge parts 26, and the cord end is introduced between the hinge parts 24 and placed in the channel formed by the sleeve-parts 24. The sleeve parts 24 herewith strive to expand, i.e. to move apart, but squeezed together still further when inserting the plug part 10 into the recess 18. This provides the desired locking effect between the plug-part 10 and the locking sleeve 12 on the one hand and between the locking sleeve 12 and the cord 20 on the other.

It will be understood that the described and illustrated embodiment of the inventive ear defender can be modified within the scope of the following claims. For instance, both the plug-part 10 and the locking sleeve may have constructions which differ widely from the illustrated and described constructions. The projections, barbs and outwardly projecting parts are suitably directed in a way which will make it difficult to separate the different components of the inventive ear defender. The numbers in which the projections, barbs and outwardly projecting parts are present can also be varied, as can also their shapes.

We claim:

1. An ear defender which comprises two ear plugs (11) each of which is connected to a respective end of a cord (20) and includes a plug-part (10) which is provided with a recess (18) for accommodating a cord locking sleeve which coacts with said plug-part, characterized in that the locking sleeve (12) has a rear end and comprises two identical sleeve-parts (24) which are joined or held together at the rear end of the locking sleeve (12) by at least one hinge or web part (26) formed integrally with the locking sleeve, wherein a length of the respective end of the cord extends into a channel (32) in the sleeve through an opening provided adjacent said hinge part and wherein said respective end of the cord is secured in the channel (32), by pressing the sleeve parts into firm engagement with said cord end within the recess (18).

2. An ear defender according to claim 1, characterized in that the hinge part (26) is constructed so that the sleeve parts (24) will strive to move away from one another.

3. An ear defender according to claim 2, characterized in that the channel (32) provided in the locking sleeve (12) is provided with inwardly facing projections (34) which are intended to grip in the cord and to hold the same securely.

4. An ear defender according to claim 2, wherein said locking sleeve has a periphery, characterized in that the locking sleeve (12) is provided around the periphery thereof with outwardly projecting parts (30) which are intended to grip that wall of the plug which faces towards the recess (18) in the plug-part (10).

5. An ear defender according to claim 2, wherein said locking sleeve has a front part, characterized in that the front part (22) of the locking sleeve (12) is conical.

6. An ear defender according to claim 2, characterized in that the plug-part (10) and the locking sleeve (12) are both made of a resilient material.

7. An ear defender according to claim 1, characterized in that the channel (32) provided in the locking sleeve (12) is provided with inwardly facing projections (34) which are intended to grip in the cord and to hold the same securely.

8. An ear defender according to claim 7, wherein said locking sleeve has a periphery, characterized in that the locking sleeve (12) is provided around the periphery thereof with outwardly projecting parts (30) which are intended to grip that wall of the plug which faces towards the recess (18) in the plug-part (10).

9. An ear defender according to claim 7, wherein said locking sleeve has a front part, characterized in that the front part (22) of the locking sleeve (12) is conical.

10. An ear defender according to claim 7, characterized in that the plug-part (10) and the locking sleeve (12) are both made of a resilient material.

11. An ear defender according to claim 1, wherein said locking sleeve has a periphery, characterized in that the locking sleeve (12) is provided around the periphery thereof with outwardly projecting parts (30) which are intended to grip that wall of the plug which faces towards the recess (18) in the plug-part (10).

12. An ear defender according to claim 11, wherein said locking sleeve has a front part, characterized in that the front part (22) of the locking sleeve (12) is conical.

13. An ear defender according to claim 11, characterized in that the plug-part (10) and the locking sleeve (12) are both made of a resilient material.

14. An ear defender according to claim 1, wherein said locking sleeve has a front part, characterized in that the front part (22) of the locking sleeve (12) is conical.

15. An ear defender according to claim 1, characterized in that the plug-part (10) and the locking sleeve (12) are both made of a resilient material.

* * * * *